United States Patent [19]

Acker et al.

[11] Patent Number: 5,752,513
[45] Date of Patent: May 19, 1998

[54] METHOD AND APPARATUS FOR DETERMINING POSITION OF OBJECT

[75] Inventors: David E. Acker; Charidimos E. Gasparakis, both of Setauket, N.Y.

[73] Assignee: Biosense, Inc., Setauket, N.Y.

[21] Appl. No.: 479,671

[22] Filed: Jun. 7, 1995

[51] Int. Cl.⁶ ..................................................... A61B 5/05
[52] U.S. Cl. ................. 128/653.1; 128/899; 324/207.11; 324/207.13; 324/207.22; 340/686
[58] Field of Search .............................. 128/653.1, 653.2, 128/897, 899; 606/130; 324/309, 207.11, 204.13, 207.17, 207.22; 378/205; 340/686

[56] References Cited

U.S. PATENT DOCUMENTS

| | | |
|---|---|---|
| 4,618,978 | 10/1986 | Cosman . |
| 4,721,914 | 1/1988 | Fukushima et al. . |
| 5,152,288 | 10/1992 | Hoenig et al. . |
| 5,198,768 | 3/1993 | Keren . |
| 5,214,615 | 5/1993 | Bauer . |
| 5,265,611 | 11/1993 | Hoenig et al. . |
| 5,377,678 | 1/1995 | Dumoulin et al. . |
| 5,383,454 | 1/1995 | Bucholz . |
| 5,517,990 | 5/1996 | Kalfas et al. . |
| 5,558,091 | 9/1996 | Acker et al. . |

*Primary Examiner*—Marvin M. Lateef
*Assistant Examiner*—Shawna J. Shaw
*Attorney, Agent, or Firm*—Lerner, David, Littenberg, Krumholz & Mentlik

[57] ABSTRACT

Apparatus for determining the position of a probe in a sensing volume includes a plurality of magnetic field generating sources for generating different magnetic fields in the sensing volume, where the sources have a planar configuration and are positioned so that they at least partially overlap one another in horizontal extent and so that the sensing volume extends outwardly from the sources. The probe is provided with sensors which detect magnetic field components of fields generated by the sources. The position of the probe can be determined from the detected magnetic components. Methods for determining the probe position are also included.

21 Claims, 5 Drawing Sheets

5,752,513

METHOD AND APPARATUS FOR DETERMINING POSITION OF OBJECT

FIELD OF THE INVENTION

The present invention relates to a method and apparatus for determining the position of an object using magnetic fields, where the object is located in a sensing volume above a plurality of overlapping magnetic field-generating sources positioned so as to overlap one another in horizontal extent. Such method and apparatus are particularly useful for monitoring the position of a probe within a human body.

BACKGROUND OF THE INVENTION

Various locating systems have been used in the past to determine the position of an object such as the tip of an endoscope or a catheter within the human body.

One problem with such locating systems, however, is that they can be quite large and expensive to construct. For example, Hoerig et al., U.S. Pat. Nos. 5,265,611 and 5,152,288, discloses a system for measuring magnetic fields emitted from a source situated within an examination subject provided within a shielded room. The walls of the shielded room are surrounded with magnetic coils to demagnetize the room. Such a system is not only expensive to construct, but requires that the patient be physically located in the shield room and therefore suffers from a lack of mobility of the apparatus.

Some magnetic locating systems require that the patient be positioned within magnetic coil openings. Although such systems can provided good locating performance, it would be desirable to provide a system which does not require coils around the patient.

Other problems exist with locating systems that use dipole far-fields, such as poor dynamic range due to fast dropping magnetic fields and sensitivity to imperfections in the coils which can create significant error. Moreover, such systems are often affected by nearby metal which acquires induced magnetism and can behave as a dipole field itself.

There is also a need for magnetic locating systems to be able to use smaller probes for insertion into the human body. Typically, the size of the probe is dependent on the size of the sensors disposed within the probe's housing. The size of the sensors is chosen, in turn, based on the sensitivity of the sensors and the strength of the magnetic field generated by the coils.

SUMMARY OF THE INVENTION

One aspect of the present invention provides apparatus for determining the position of an object comprising a plurality of magnetic field generating sources for generating a plurality of different magnetic fields in a sensing volume. The sources each have a substantially planar configuration and are positioned so as to at least partially overlap one another in horizontal extent, with the sensing volume extending outwardly from the sources.

The apparatus further includes control means for actuating the sources to generate magnetic fields in a predetermined sequence, a sensor connected to the object and movable within the sensing volume, and adapted to detect magnetic field components in at least two different local directions relative to the sensor, and calculation means for determining the position of the sensor from the magnetic field components detected by the sensor during generation of the magnetic fields.

Preferably, the apparatus also includes control means for generating a plurality of successive magnetic fields within the sensing volume to actuate the sources to generate the magnetic fields in sequence. In this case, the calculation means are desirably operative to determine the position of the probe within the sensing volume from the magnetic field components detected during generation of the magnetic fields.

The magnetic field generating sources are preferably formed from a plurality of conductor segments, and the calculation means calculates the magnetic field contribution B of each conductor segment in accordance with the equation:

$$|B(x,y,z)|=I(\cos(A1)+\cos(A2))/(cR)$$

where I is the current through the conductor segment, c is the speed of light, R is the distance between the location of the sensor at point r=(x,y,z) and the conductor segment, A1 is the angle between the sensor and one end of the conductor segment, and A2 is the angle between the sensor and the other end of the conductor segment.

In terms of shape, the conductor segments of each source are preferably polygonal in shape, and more desirably comprise isosceles triangles. Three sources or more preferably four sources are employed by the present invention. The sources can further be arranged to overlap one another in horizontal extent to produce a eight-pointed star, and include center points which are spaced apart from one another at a center distance, preferably about 10 cm. The conductor segments are rectangular in cross-section.

Preferably, the sensing volume extends outwardly to a maximum distance of interest, and the ratio of the maximum distance of interest to an effective diameter of the sources is less than or equal to two, where the effective diameter comprises a diameter of a circle circumscribing the sources.

According to another aspect of the invention, the plurality of sources comprises at least two sources, and the apparatus further includes dipole means for generating one or more magnetic dipole fields within the sensing volume. In this aspect, the calculation means are further operative to determine the position of the probe within the sensing volume from magnetic field components detected by the sensor during generation of the magnetic fields by the sources and magnetic field components detected by the sensor from the dipole means.

In yet another aspect of the present invention, apparatus for determining the position of an object includes a plurality of magnetic field generating sources for generating a plurality of different magnetic fields in a sensing volume. The sources each have a planar configuration and include conductors encompassing an enclosed area. The sources are positioned so as to at least partially overlap one another in horizontal extent and define an overlap area, the overlap area encompassing at least about fifty percent of the enclosed area of each source, and the sensing volume extending outwardly from the sources in the vicinity of the overlap area. The apparatus also includes control means for actuating the sources to generate the magnetic fields in a predetermined sequence, a sensor connected to the object and movable within the sensing and adapted to detect magnetic field components in at least two different local directions relative to the sensor, and calculation means for determining the position of the sensor from the magnetic field components detected by the sensor during generation of the magnetic fields.

Further aspects of the invention provide methods of determining the position of an object within a sensing volume. Methods according to this aspect include the steps of actuating a plurality of magnetic field-generating sources having a substantially planar configuration being positioned so as to partially overlap one another in horizontal extent to generate a plurality of magnetic fields in a predetermined sequence such that at least two of the sources generate fields varying quasi-linearly with position within near-field volumes, the near-field volumes of the intersecting one another within a sensing volume extending outwardly from the sources. The method further includes the steps of measuring magnetic field components in the sensing volume above the near-field areas of the sources in at least two different local directions relative to a sensor connected to the object during generation of the fields, and determining the position of the sensor from the magnetic field components detected during generation of the magnetic fields.

Preferably, the sources are formed from a plurality of conductor segments, and the step of determining the position of the sensor includes the step of calculating magnetic field contributions of each of the conductor segments of the sources. In one aspect, the step of calculating comprises calculating the magnetic field contribution B of each the conductor segment in accordance with the equation $|B(x,y,z)|=I(\cos(A1)+\cos(A2))/(cR)$ described above.

Further aspects of the invention provide methods of determining the position of an object within a sensing volume including the steps of generating a plurality of different magnetic fields in a predetermined sequence in the sensing volume from a plurality of magnetic field generating sources each having a substantially planar configuration and positioned so as to at least partially overlap one another in horizontal extent, measuring magnetic field components of the magnetic fields generated from the plurality of sources in at least two different local directions relative to a sensor connected to the object during generation of the fields, and determining the position of the sensor from the magnetic field components detected during generation of the magnetic fields.

Yet future aspects of the invention provide methods of determining the position of an object within a sensing volume including the steps of generating a plurality of different magnetic fields in a predetermined sequence in the sensing volume from a plurality of magnetic field generating sources each having a substantially planar configuration and being positioned so as to at least partially overlap one another in horizontal extent, generating one or more magnetic dipole fields within the sensing volume, measuring magnetic field components of the generated magnetic fields in at least two different local directions relative to a sensor connected to the object during generation of the fields, and determining the position of the object from the magnetic field components detected during generation of the magnetic fields.

The foregoing and other objects, features and advantages of the present invention will be more readily apparent from the detailed description of the preferred embodiments set forth below, taken in conjunction with the accompanying drawings.

DETAILED DESCRIPTION OF PREFERRED EMBODIMENTS

Figure 1:
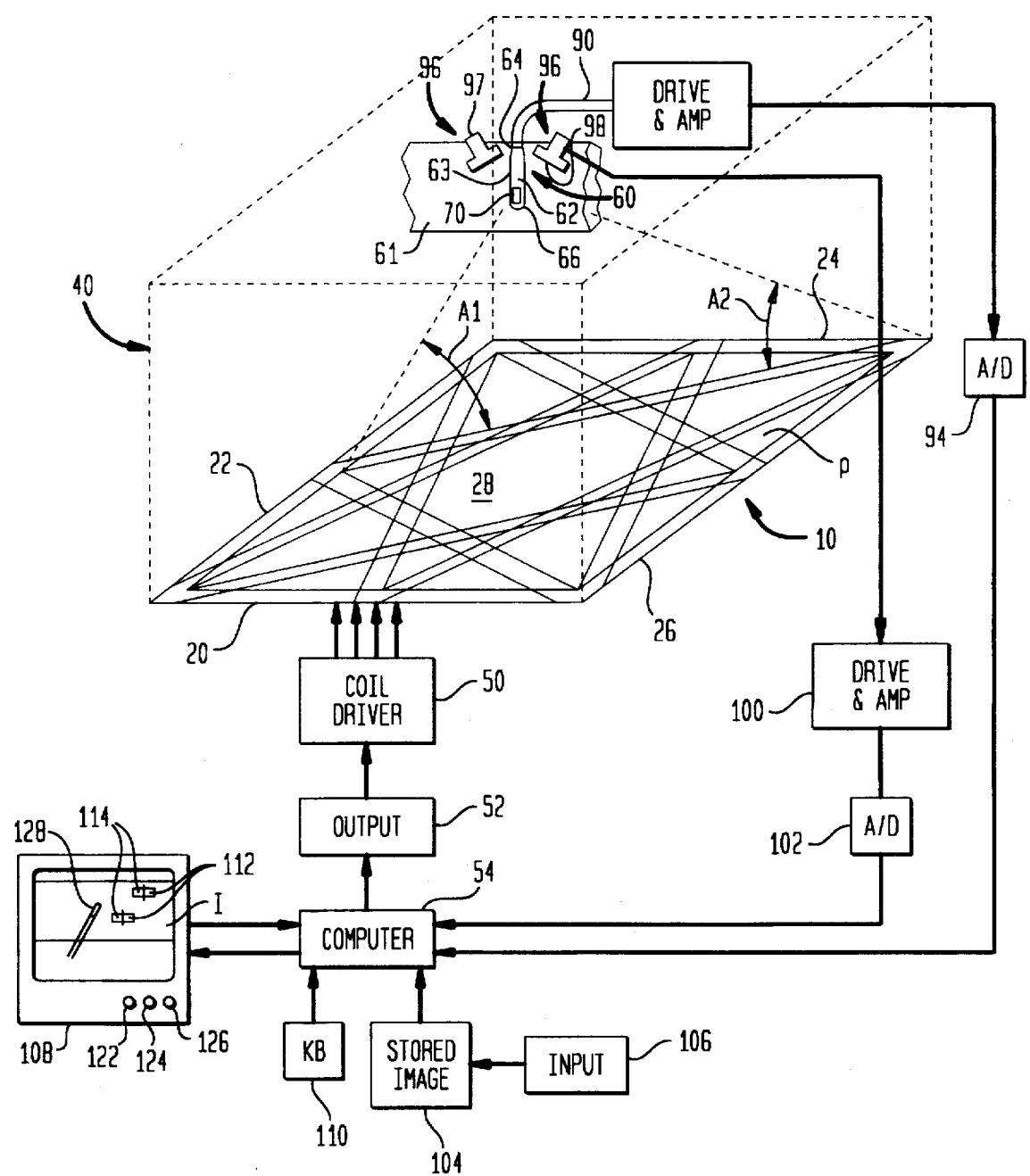
FIG. 1 is a diagrammatic, perspective view of a portion of apparatus in accordance with one embodiment of the present invention.
Figure 2:
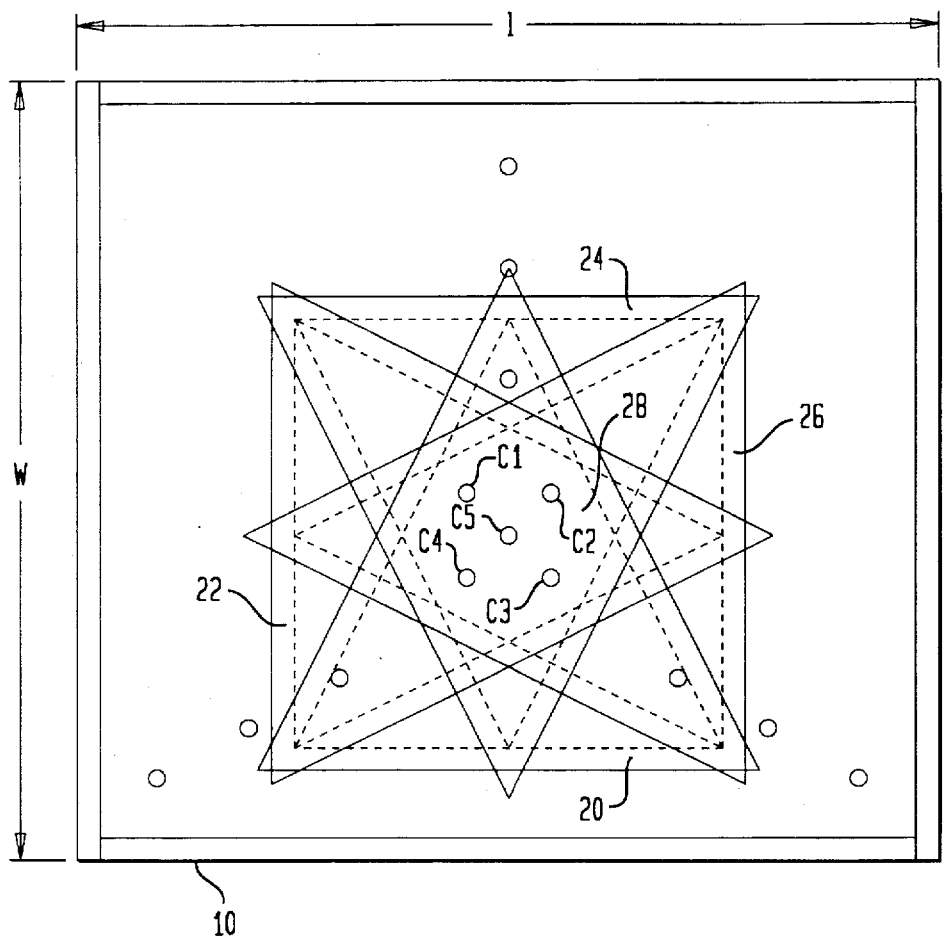
FIG. 2 is a top view of apparatus in accordance with a preferred embodiment of the present invention.
Figure 3:
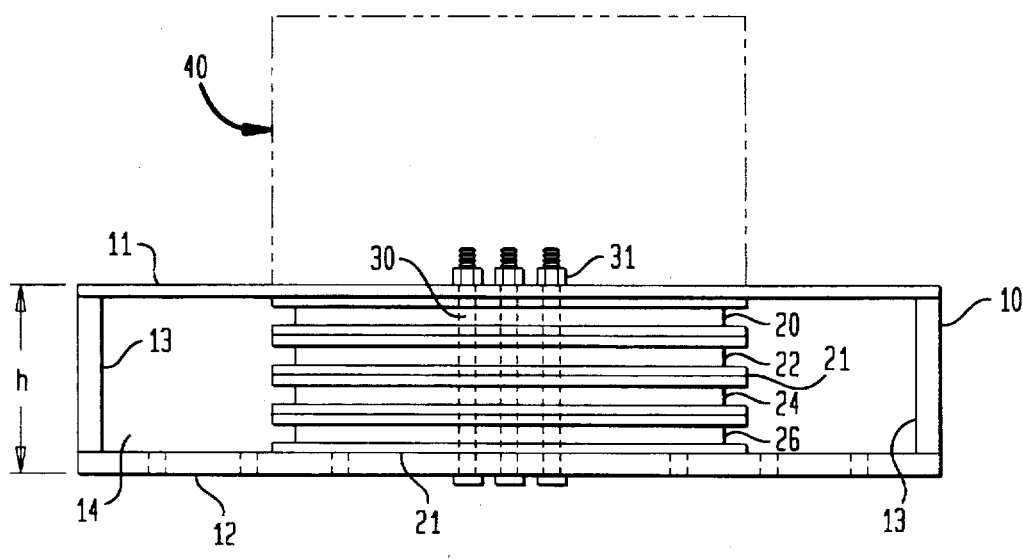
FIG. 3 is a side view of the apparatus shown in FIG. 2.

Referring to FIGS. 1–3, apparatus in accordance with a preferred embodiment of the present invention includes a frame structure 10 which primarily extends horizontally along the X-Y plane of an X-Y-Z coordinate system with a length L and width W. Frame structure 10 also has an associated height H which extends along the Z-axis. Preferably, the length L and width W of frame structure 10 extending in the X-Y plane is significantly larger in dimension than the height H along the Z-axis such that frame structure 10 can be considered substantially planar in the X-Y plane. Although the dimensions of the frame structure 10 can vary according to the particular application, preferred dimensions include a height H of about 10 cm, a width W of about 70 cm and a length L of about 70 cm.

Frame structure 10 supports a plurality of magnetic field generating sources or coils 20, 22, 24, and 26 which are preferably positioned on top of the other such that they overlap in a horizontal extent, i.e., the coils all extend substantially in horizontal X-Y planes such that from a viewpoint form above the coils, they are overlapping one another. Preferably, all of the coils overlap one another to provide an overlapping region 28 as shown in FIG. 2.

Figure 4:
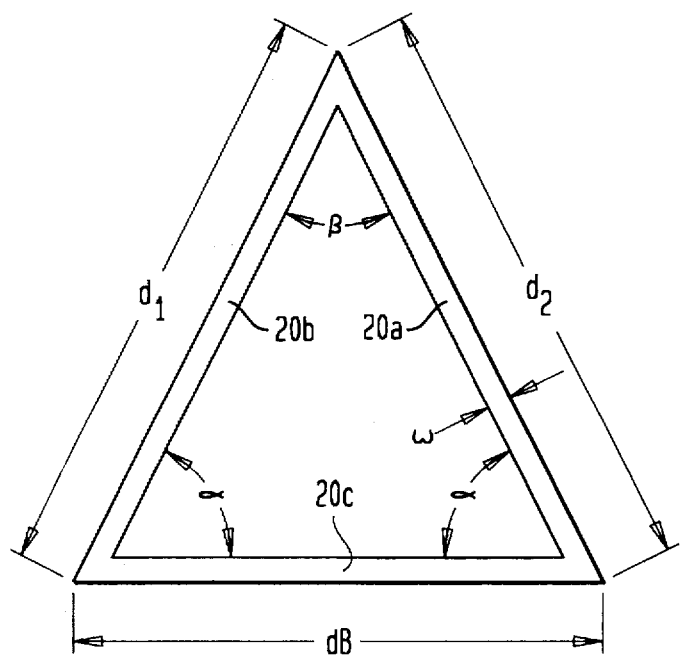
FIG. 4 is a top view of a portion of apparatus in accordance with one embodiment of the present invention.
Figure 5:
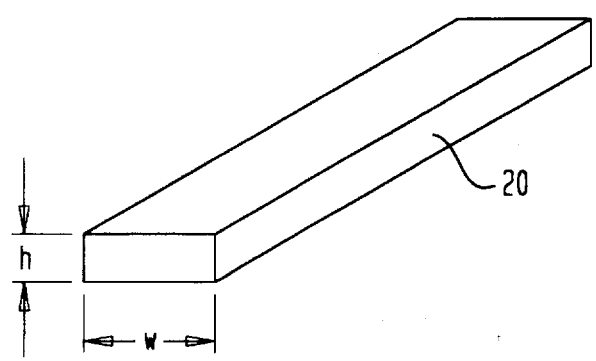
FIG. 5 is a side view of the portion of apparatus shown in FIG. 4.

In a preferred embodiment, all of the coils are isosceles triangles where each coil comprises two side segments which are equal in length. Referring to FIGS. 4 and 5, a single coil 20 is shown with side segments 20a, 20b and 20c. Preferably, the outside distances d1 and d2 are equal in length and are preferably between 64.8 and 91.6 cm, which outside distance d3 is slightly less than the distances d1 and d2 by about 58.0 to 82.0 cm. The width w of each segments is preferably between 2.5 and 3.5 cm and the height h of each segment is between 0.952 and 1.346 cm.

The angles α formed between segments 20a and 20c and between segments 20b and 20c are preferably equal and measure approximately between about 64.43 degrees. The angle β between segments 20a and 20b measures between about 53.14 degrees. Although in a preferred embodiment each coil is an isosceles triangle, equilateral or scalene triangles may also be used and each coil need not be identical in shape in size, although this is clearly preferred from a calculations standpoint.

Frame 10 is preferably constructed from a nonmagnetic material and preferably formed from polymers such as polycarbonates, polyamides such as nylons, polyethers, etc. For example, frame 10 can be formed from clear Plexiglas material so as to allow viewing of the coils inside. Frame 10 comprises top wall 11, bottom wall 12, and side walls 13 defining an interior 14 within frame 10. Interior 14 houses coils 20, 22, 24, and 26 which are positioned on top of one another and separated by spacing plates 21 positioned above and below each coil. Spacing plates 21 are preferably formed from a nonmagnetic material and extend along the X-Y plane. The coils are arranged so as to create common overlapping regions in the horizontal extent such as overlapping region 28, as shown in FIG. 2. Frame 10 and coils 20, 22, 24, and 26 are preferably secured together using nonmagnetic fastening bolts 30 and nuts 31, which extend from bottom wall 12 of frame 10 through top wall 11. Of course, it should be appreciated that other suitable fastening means may be used to secure the coils and the frame.

Referring to FIG. 2, the centers c1, c2, c3, and c4 of coils 20, 22, 24, and 26 are shown. Preferably, the centers c1–c4 are spaced apart from one another by at least 0.5 to 15 cm and are preferably spaced apart at a distance s of approximately 10 cm. The spacing of the centers of the coils apart form one another is important to the operation of the apparatus as will be described below and determined by the particular geometry of the coils.

A sensing volume 40 includes the region of space extending outwardly from the frame structure 10 along the Z-axis. Sensing volume 40 preferably extends outwardly from frame 10 such that the ratio of the maximum distance of interest extending along the Z axis to the effective diameter of the coils is less than or equal to two, where the effective diameter of the is the diameter of a circle which circumscribes all of the coils. However, the larger the distance between the centers of the coils, the larger the ratio would be. Thus, generally the sensing volume should have a maximum height along the Z-axis which is relatively small compared to the span of coils along the X-Y plane.

Figure 7A:
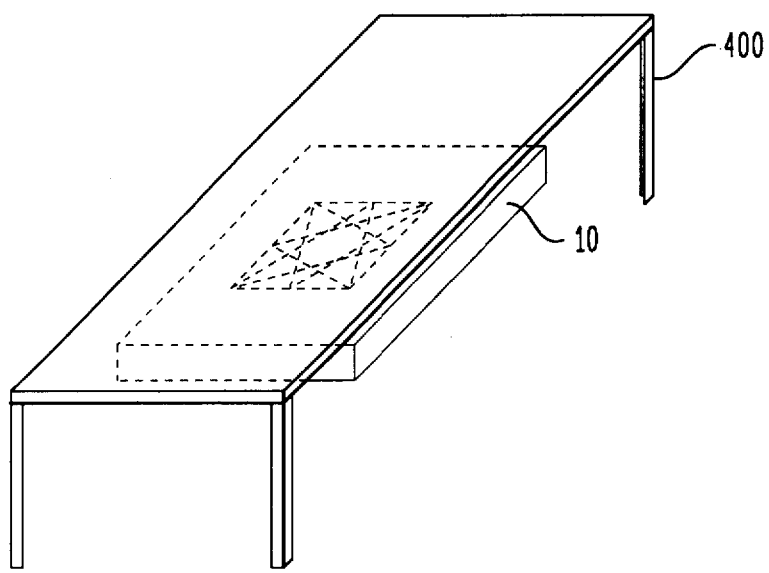
FIG. 7A is a perspective view showing a portion of the apparatus shown in FIG. 1 in an under-bed arrangement.
Figure 7B:
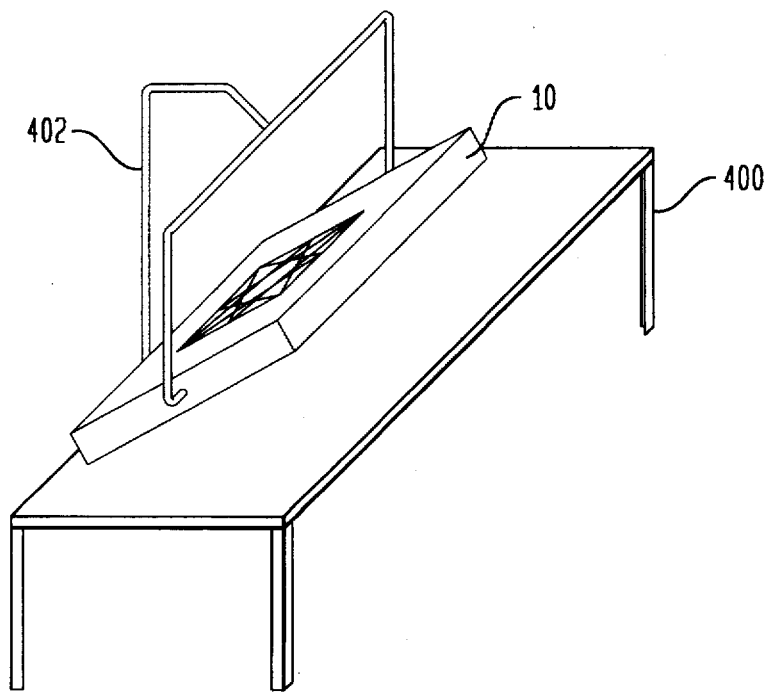
FIG. 7B is a perspective view showing a portion of the apparatus shown in FIG. 1 is an above-bed arrangement.

Frame 10 and coils 20, 22, 24, and 26 are constructed so as to permit the introduction of a body part of a living patient within sensing volume 40. Preferably, as shown in FIG. 7A, frame 10 can be located in an "under bed" position just below the surface of an operating table 400 on which a patient can be placed. Advantageously, frame 10 can be positioned in numerous other ways, such as sideways or above the patient, as shown in FIG. 7B in which case sensing volume 40 would extend downwardly towards the patient who would be positioned below frame 10. One can easily see the benefits of using such a system which has high positioning versatility and mobility. For instance, frame 10 could be placed on a mobile assembly 402 thereby allowing it to be moved from room to room within a hospital and positioned over a patient who must remain immobilized and cannot be moved onto an operating table.

Referring to FIG. 1, all of the coils are connected to a common coil driver 50 which is in turn connected via an output interface 52 to receive output from a computer 54. Computer 54 may be a digital computer of the type commonly referred to as a workstation or dedicated computer. Output interface 52 is arranged to accept command signals from computer 54 and actuate coil driver 50 in response to such commands. Coil driver 50 includes a conventional DC power supply and conventional switching devices for connecting the coils 20, 22, 24 and 26 to the power supply of the coil driver in sequence. The coils are connected to the coil driver such that current can be passed through each coil.

The apparatus further includes a patient monitoring probe 60 which includes an elongated body 62 having a proximal end 64 and a distal end 66 adapted for insertion into a body part 61 of the patient. In the particular embodiment illustrated, the probe body 62 is an elongated, flexible shaft adopted to fit inside an endoscope 63 which may be introduced into the body. The endoscope 63 has one or more bores or passageways for conducting surgical instruments, fluids, and the like so as to introduce the same into the patient's body, and probe body 62 may fit within one such bore. Such bores or passageways may also be used for the passage of endoscopic surgical instruments or other treatment devices or substances. Alternatively, probe body 62 or endoscope 63 may include other electrical, optical, or electrooptical devices for providing a local image of the tissues surrounding distal end 66 such as video cameras and fiber optic bundles. The endoscope may be connected to conventional medical treatment apparatus for introducing and/or withdrawing fluids, for observing the tissues surrounding the tip by means of the electrical or the electrooptical devices and for performing other conventional medical treatment applications commonly performed through probes that are inserted into the human body.

Figure 6:
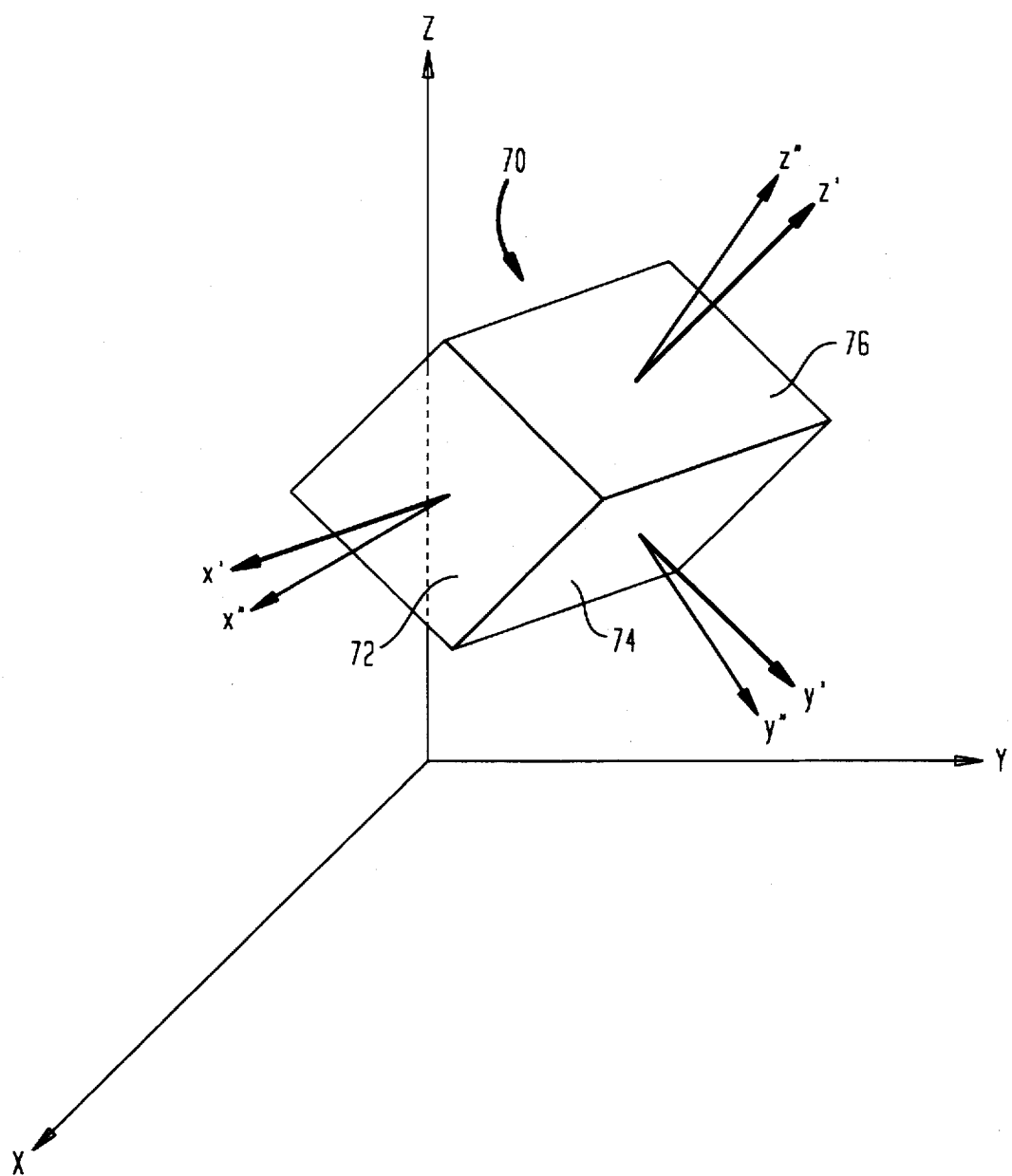
FIG. 6 is a diagrammatic view depicting a portion of the apparatus shown in FIG. 1.

A sensor 70 is mounted to probe body 62 adjacent the distal end 66. As best seen in FIG. 6, sensor 70 includes a plurality of planar sensing elements 72, 74, and 76 disposed in a reference frame or laboratory spanned by XYZ axes. Ideally, elements 72, 74 and 76 of sensor 70 are mutually orthogonal with respect to one another and defining an ideal sensor reference frame spanned by axes X'Y'Z' where element 72 is arranged normal to ideal sensor axis X', element 74 is arranged normal to ideal sensor axis Y' and element 76 is arranged normal to ideal sensor axes Z'. However, in actuality, the elements 72, 74 and 76 of sensor 70 may have angular offsets from the ideal orthogonal sensor axes which must be accounted for to ensure accuracy. These offsets can be determined by measurement of the angular deviation of the sensing elements from the orthogonal axes. Thus, elements 72, 74, 76 may be actually offset from orthogonal axes X'Y'Z' and arranged normal to non-orthogonal axes X"Y"Z" defining a sensor offset reference frame as shown in FIG. 6. Using this coordinate system, sets of unit vectors can be defined that span the XYZ reference axes, the X'Y'Z' ideal sensor axes and the X"Y"Z" sensor offset axes. Thus, unit vectors $e_l[1]$, $e_l[2]$, $e_l[3]$ span orthogonal reference axes XYZ, unit vectors $e_p[1]$, $e_p[2]$, $e_p[3]$ span orthogonal ideal sensor axes X'Y'Z' and unit vectors $e_n[1]$, $e_n[2]$, $e_n[3]$ span non-orthogonal sensor offset axes X"Y"Z".

The orientation of the sensor with respect to the XYZ coordinate system can be expressed in many ways. Preferably, however, the orientation is expressed as three angles referred to as pitch, roll and yaw. All three angles are referenced to an assumed "home" or zero position in which the X'Y'Z' ideal local directions of the sensor are aligned with the XYZ directions of the frame structure spanned by the XYZ axes. Referring to reference frame XYZ, pitch is shown as the angle P spanned as the frame is rotated along the X-axis, yaw results form rotation about the Z-axis, pitch is measured from the first rotation a s rotation about the Y-axis, and roll is measured from the second rotation as rotation about the X-axis. Any other internally consistent set of angles could be also be used to specify orientation of the sensor. Moreover, the orientation of the sensor can be fully specified by specifying any two unit vectors of the sensor local coordinate system in terms of the XYZ and X'Y'Z' reference coordinate systems.

Because the sensor is disposed in the distal tip 66 of sensor 60, the position and orientation of sensor 70 are not fixed with respect to the XYZ reference axes. Thus, the local axes X"Y"Z" of sensor 70, in addition to being offset with respect to ideal sensor axes X'Y'Z', can be offset at any orientation with respect to the XYZ reference axes spanning the sensing volume.

Generally, the position and location of the sensor are ascertained as magnetic fields generated by the coils are switched on and off in the sequence and each sensor measures a value of the magnetic flux sensed at the sensor's location at preselected acquisition times corresponding to activation times of each of the field-generating coils. Each coil generates a field in space that is functionally known. For example, in the case of triangular coils, as each coil is switched on, the magnetic field generated is the linear superposition of the field generated from the three conductor segments which comprise the coil, and the magnitude of this field can be calculated as:

$$|B(x,y,z)|=I(\cos(A1)+\cos(A2))/(cR)$$

where R is the distance between the location of the sensor at point r=(x, y, z) and the conductor segment, I is the current flowing through the conductor segment, c is the speed of light, A1 is the angle between the sensor and one end of the conductor segment, and A2 is the angle between the sensor and the other end of the conductor segment (see FIG. 1).

The coils are repeatedly activated and at predetermined intervals the components of the field in the X", Y", and Z" direction of sensor 70 are obtained during each coil activation. Similarly, the magnetic flux component values from at least two reference points are acquired for each cycle of the coils to derive the position and orientation of the reference points as well.

The location of the probe within the XYZ reference frame is determined by an equation solving technique which equates the measured field values to theoretical field values at a given position. Given the measured values of the magnetic filed components for each coil activation mode, a system of overdetermined equations are derived which equates the measured values of the field component to the general functional or theoretical form that such a value should possibly have. In the case of four triangular coils, there would be twelve non-linear equations (three equations for each coil activation mode) with six unknowns including the position vector of the probe (3 unknowns) and its orientation expressed as roll, pitch and yaw angles (3 unknowns). As described below, these equations can be solved using a standard non-linear least squares minimization algorithm or by any other known method of solving systems of overdetermined equations.

The leads of sensor 70, including lead 90 and other leads associated with other sensing elements (not shown), are connected to a drive and amplification unit 92 via cable 90 extending through the body 62 of probe 60. Drive and amplification unit 92 is arranged to apply all of the appropriate excitation voltages to the elements of sensor 70 and to amplify the output voltages of the various sensing elements. The drive and amplification unit 92 is connected to an analog-to-digital (A/D) converter 94 which in turn is connected to an input of computer 54. Although only a single connection is shown, it should be appreciated that A/D converter 94 is a multi-channel device, with multiple connections and/or with multiplexing arrangements for delivering digital representations of all of the output signals from all of the sensing elements in sensor 70 to computer 54.

The apparatus further includes two or more fiducial markers 96 each which incorporates a sensor 97 and a marker body 98. Marker body 98 is arranged for mounting to a body part 61 of a patient in a substantially fixed position relative to such body part. Thus, marker body 98 can incorporate clamps, bands, rings, or straps for fastening it onto the exterior of the patient's head, limb, or torso for example. Alternatively, body 98 may include apertures or notches to accommodate sutures, pins, surgical staples or other fastening devices. The body of fiducial marker 96 may also be fastened to the patient's body with conventional surgical adhesive tape, bandages or the like. At least one part of the fiducial marker, such as marker body 98, the sensor 97, or both, is formed from a material which is detectable in a patient by imaging technique such as X-ray, magnetic resonance imaging (MRI), computerized axial tomography (CAT) or other commonly used imaging techniques. Sensor 97 of fiducial marker 96 is substantially the same as sensor 70 of the probe 60. Sensor 97 is connected to a drive and amplification unit 100, which is in turn connected through an A/D converter 102 to computer 54. Units 100 and converter 102 are similar to drive and amplification unit 92 and A/D converter 94.

The apparatus further includes an image storage unit 104 for storing an image of a patient or of a body part of a patient in digital form. Typically, image storage unit 104 includes conventional computer memory devices. An image input device 106 is also provided, which may include conventional digital data input devices such as a disk drive, data compression link, or the like for accepting images in digital form permitting suitable imaging equipment such as X-ray equipment, MRI, CAT, or video equipment to transfer the input images into image storage device 106. A display monitor 108 is also linked to computer 54 for displaying visual images. The data input devices to computer 54 may also include a mouse, track ball, joy stick (not shown) and/or keyboard 110.

In a method according to one embodiment of the invention, the body part of the patient, such as the arm, is imaged using conventional imaging apparatus such as MRI, CAT, X-ray or the like, while fiducial markers 96 are mounted on the body part. Thus, the image data so required includes a depiction of the fiducial markers. In this regard, it is not essential that the fiducial markers be mounted on the patient's body part at this stage of the process.

After this imaging step, the fiducial markers remain in place on the patient throughout the remainder of the process. The image data depicting the patient's body part, including the depiction of fiducial markers 96, is transferred through input device 106 to image storage unit 104. The image data may include an image in a single plane, or, more desirably, images in plural planes or a fully three-dimensional image, such as a map of the radioopacity or magnetic resonance activity over a full three-dimensional volume incorporating a portion of the body part. The image data may be stored as output data wherein individual data elements represent densities or colors to be displayed on a pictorial representation of the image. Alternatively, the image may be stored in the form of input data such as time domain or frequency domain representations of magnetic resonance signals, or unprocessed tomographic data, from which a pictorial representation can be reconstructed.

In the next stage, the body part of a patient is positioned within sensing volume 40. Probe 60 is then advanced into the patient's body using conventional techniques of the medical arts. Computer 54 actuates coil driver 50 to operate the coils in a predetermined, repetitive sequence. This sequence includes a null state, in which all of the coils are turned off and only the magnetic fields in the sensing volume 40 are those introduced by extraneous sources, such as the earth's magnetic field, stray magnetic fields from nearby items, and the like.

As the magnetic fields are switched on and off in the sequence, computer 54 controls acquisition of data from sensors 70 and 96 so that the signals representing each field are acquired at a preselected acquisition time during each switching cycle. Thus, as each coil is switched on, the magnetic field generated by each triangular coil is the linear superposition of the field generated from the three conductor segments which comprise the coil. The magnitude of this field can be calculated as:

$$|B(x,y,z)|=I(\cos(A1)+\cos(A2))/(cR)$$

where R is the distance between the location of the sensor at point r=(x,y,z) and the conductor segment, I is the current flowing through the conductor segment, c is the speed of light, A1 is the angle between the sensor and one end of the conductor segment, and A2 is the angle between the sensor and the other end of the conductor segment.

While the coils are repeatedly activated, signals are obtained through sensors 70 and 96, amplified, digitized, and fed to computer 54. The signals are then used to ascertain the orientation and position of the sensor, and the attached probe, within sensing volume 40, in the XYZ coordinate system. At each stage of each cycle, computer 54 acquires data representing the component of the magnetic field of each sensor element so that there is a separate data entry for the field during each coil activation. In exactly the same way, the computer acquires magnetic flex component values from the sensing elements of sensor 97 on fiducial markers 98. On each cycle of the coils, the computer in sequence derives the position and orientation of the fiducial markers as well.

Computer 54 takes the data defining the image of the patient's body part from storage device 104 and displays a pictorial representation of the image on monitor 108. Because the image of the patient's body part acquired during the imaging step includes a depiction of fiducial markers 97, the displayed image I will include a pictorial depictions 112 of fiducial markers 97. The computer also actuates monitor 108 to display pictorial representations 114 of the fiducial markers 97 at a location on the monitor screen. Representations 114 are displayed at positions corresponding to their positions in the XYZ frame of reference, i.e., to the positions of the fiducial markers as derived from the magnetic field measurements. The orientation of representations 114 is said to correspond to the orientation of the fiducial markers determined from the magnetic field of measurements. If the representations 114 of the fiducial markers are in registration with depictions 112 of the same markers on the monitor screen, this indicates that the image of the patient's body part is displayed at a location and/or orientation on the monitor screen corresponding to the location and orientation of the body part within the XYZ reference coordinate system.

Registration of the image I with the fiducial markers can be accomplished as follows. First, it is assumed that the coordinates of three fiducial points in image data coordinate system (image position) are known:

$$\{(Mx1, My1, Mz1), (Mx2, My2, Mz2), (Mx3, My3, Mz3)\},$$

and also the coordinates of these three fiducial points in posometer lab coordinate system (posometer position):

$$\{(Px1, Py1, Pz1), (Px2, Py2, Pz2), (Px3, Py3, Pz3)\}$$

Fiducial points $\{(x1, y1, z1), (x2, y2, z2), (x3, y3, z3)\}$ can be formed by $\{(a1, b1, c1), (a2, b2, c2), (a3, b3, c3)\}$ through rotation R and translation T. The rotation matrix R is:

$$R = \begin{bmatrix} Rxx & Ryx & Rzx \\ Rxy & Ryy & Rzy \\ Rxz & Ryz & Rzz \end{bmatrix}$$

where $Rxx = \cos(\alpha) \times \cos(\gamma) - \sin(\alpha) \times \sin(\beta) \times \sin(\gamma)$ $Rxy = \cos(\alpha) \times \sin(\gamma) + \sin(\alpha) \times \sin(\beta) \times \cos(\gamma)$ $Rxz = -\sin(\alpha) \times \cos(\beta)$ $Ryx = -\cos(\beta) \times \sin(\gamma)$ $Ryy = \cos(\beta) \times \cos(\gamma)$ $Ryz = \sin(\beta)$ $Rzx = \sin(\alpha) \times \cos(\gamma) + \cos(\alpha) \times \sin(\beta) \times \sin(\gamma)$ $Rzy = \sin(\alpha) \times \sin(\gamma) - \cos(\alpha) \times \sin(\beta) \times \cos(\gamma)$ $Rzz = \cos(\alpha) \times \cos(\beta)$ The translation matrix T is:

$$T = \begin{bmatrix} x & y & z \\ x & y & z \\ x & y & z \end{bmatrix}$$

The relationship between image position and posometer position is:

$$\begin{bmatrix} Mx1 & My1 & Mz1 \\ Mx2 & My2 & Mz2 \\ Mx3 & My3 & Mz3 \end{bmatrix} R + T = \begin{bmatrix} Px1 & Py1 & Pz1 \\ Px2 & Py2 & Pz2 \\ Px3 & Py3 & Pz3 \end{bmatrix} \text{ or}$$

$$\begin{bmatrix} Mx1 & My1 & Mz1 \\ Mx2 & My2 & Mz2 \\ Mx3 & My3 & Mz3 \end{bmatrix} R + T - \begin{bmatrix} Px1 & Py1 & Pz1 \\ Px2 & Py2 & Pz2 \\ Px3 & Py3 & Pz3 \end{bmatrix} = \begin{bmatrix} 0 & 0 & 0 \\ 0 & 0 & 0 \\ 0 & 0 & 0 \end{bmatrix}$$

This forms 9 single equations:

$Mx1 \times Rxx + My1 \times Rxy + Mz1 \times Rxz + x - Px1 = 0$ $Mx1 \times Ryx + My1 \times Ryy + Mz1 \times Ryz + y - Py1 = 0$ $Mx1 \times Rzx + My1 \times Rzy + Mz1 \times Rzz + z - Pz1 = 0$ $Mx2 \times Rxx + My2 \times Rxy + Mz2 \times Rxz + x - Px2 = 0$ $Mx2 \times Ryx + My2 \times Ryy + Mz2 \times Ryz + y - Py2 = 0$ $Mx2 \times Rzx + My2 \times Rzy + Mz2 \times Rzz + z - Pz2 = 0$ $Mx3 \times Rxx + My3 \times Rxy + Mz3 \times Rxz + x - Px3 = 0$ $Mx3 \times Ryx + My3 \times Ryy + Mz3 \times Ryz + y - Py3 = 0$ $Mx3 \times Rzx + My3 \times Rzy + Mz3 \times Rzz + z - Pz3 = 0$ with 6 unknowns: $\alpha$, $\beta$, $\gamma$ for rotation angles, x, y, z for space translation. The registration procedure is to find rotation angles $\alpha$, $\beta$, $\gamma$ and space translation x, y, z by solving the above 9 equations. In pseudo-code, the registration procedure is:

```
registration ( )
    Initialize data buffer;
    Assign fiducial reference points to image data (usually 3 points);
    Initialize posometer system;
    Measure lab positions of the chosen fiducial points;
    Apply equation solving method (non-linear least square) on
        equations, and find rotation angles α, β, γ and space
        translation x, y, z;
    Form rotation matrix R from α, β, γ and translation matrix T
        from x, y, z;
```

The rotation matrix R and translation matrix T can then be applied to subsequent positions obtained.

The particular image I shown in FIG. 1 is an image taken on a cutting plane parallel to the Y-Z axes. If the position and orientation data for the fiducial markers 97 derived from the magnetic field measurements indicates that the patient's body part has moved by in the +Y direction and has rotated clockwise around the +X axes since the image was initially brought into registration, then computer 54 will transform the image and actuate monitor 108 to show the image displaced and rotated in the corresponding directions on the monitor screen. Methods of transforming stored images to show displacements and rotations in two and three dimensions are well known in the art, and need not be described in detail here. However, such methods are commonly employed to show the image transformed in response to arbitrarily input displacements and positions. Here, the transformation techniques are applied in response to true displacements and rotations of the body part measured by the magnetic field monitoring system.

At this point, the image I of the patient's body part is displayed on the screen of monitor 108 in a position corresponding to its true position and orientation in the XYZ reference coordinates of the reference frame and coils. The computer actuates display 108 to show a representation 128 of at least the distal end 66 of the probe 60. The position and orientation of representation 128 correspond to the position and orientation of the distal tip 66 derived from magnetic field measurements by sensor 70. As both the representation 128 and the image I are displayed on monitor 108 in positions and orientations corresponding to the true position and orientation of the probe and of the patient's body part in the XYZ reference direction coordinate system, the combined representation 128 and image I on the monitor screen accurately depict the position of the probe distal tip 66 relative to the patient's body part. Also, as the position and orientation of probe distal tip 66 changes, the computer will alter the position and orientation of the probe representation 128 on the monitor screen. The representation of the monitoring probe tip 66 and of fiducial markers 96 may be pictorial representations or else may be schematic representations such as lines, arrows or the like.

Thus, the system will continually show the true relationship between the probe tip and the patient's body part. In effect, the system provides a result similar to that which would be achieved by continually imaging the patient during the medical procedure, as by continually taking X-ray, CAT, or MRI images to show the probe tip. However, the magnetic field monitoring steps according to this embodiment of the invention do not interfere with the ongoing medical procedure. No ionizing radiation is employed.

The triangular coils are arranged so that the system operates in the "near-field," i.e., the field within the collective areas of the overlapping coils. Preferably, near-field operation is most effective when the ratio of the maximum distance of interest within the sensing volume to the "effective diameter" of the coils is not larger than two, where the effective diameter is the diameter of a circle which circumscribes the coils. This ratio allows the use of much smaller driving currents as compared to driving currents used to drive smaller coils producing very fast dropping dipole fields.

It is also preferable to minimize the total area of the system while maximizing the distances among the centers of the coils. The centers of the coils should be spaced apart from one another since for similarly-shaped coils the more the coils coincide with one another, the more they tend to behave as one coil, in which case information will be lost. In addition, common centers for non-similarly shaped coils can produce potential singularity problems where two or more points in the region of interest produce equal fields or fields of equal magnitudes for all coil activation modes. Therefore, it is preferable to employ isosceles triangular coils such that if the bases of the coils are positioned along sides of a square, there will be an offset of the centers of each coil with respect to the other coils.

The triangular shape of the coils is preferred to other polygonal shapes for a number of reasons. For instance, overlapping triangles, as opposed to similarly overlapping higher order polygons, provided the largest coil to coil difference in their fields on average over the volume of interest. Triangular shaped coils, however, need not be exclusively used and other polygonal shapes can be use, such as rectangles, pentagons, hexagons, etc. In addition, even circular coils can be used. In addition, although four sources or coils are preferred, three coils can be used as well as two planar coils and one or more dipole sources.

In operation, the probe is placed in a magnetic field produced by each coil and therefore each sensor of the probe measures a value of the magnetic flux at the probe's position.

Provided that the physical configuration of the field generator is known (e.g., triangle coils) which is fixed in position during operation, the magnetic field detected by a sensor is a function of the position and orientation of the sensor. The field generator coils are stimulated sequentially, and the field sensed by a sensor (3 sensors per probe) can be expressed in terms of position in x, y, z and orientation $\alpha$, $\beta$, $\gamma$ (roll, pitch and yaw respectively) i.e., $$B[sensor][coil]=f[sensor][coil](x, y, z, \alpha, \beta, \gamma)$$

If the real field the sensor measures when coil is on is B'[sensor][coil], then theoretically, $$B'[sensor][coil]=B[sensor][coil]$$

i.e., $$B'[sensor][coil]-f[sensor][coil](x, y, z, \alpha, \beta, \gamma)=0.0$$

Since there are 3 sensors and 4 coils, the total equations are 12 with 6 unknowns (x, y, z for probe space location, $\alpha$, $\beta$, $\gamma$ for its orientation). By applying non-linear least square method, the unique x, y, z, $\alpha$, $\beta$, $\gamma$ for the probe can be found.

More specifically, assuming the orthogonal XYZ reference coordinate system (lab Cartesian coordinate) is described by matrix:

$$e_l = \begin{bmatrix} e_{l11} & e_{l12} & e_{l13} \\ e_{l21} & e_{l22} & e_{l23} \\ e_{l31} & e_{l32} & e_{l33} \end{bmatrix}$$

the probe's orthogonal system is:

$$e_p = \begin{bmatrix} e_{p11} & e_{p12} & e_{p13} \\ e_{p21} & e_{p22} & e_{p23} \\ e_{p31} & e_{p32} & e_{p33} \end{bmatrix}$$

and, since the three sensors on probe may not be orthogonal to each other, their non-orthogonal axes can described as:

$$e_n = \begin{bmatrix} e_{n11} & e_{n12} & e_{n13} \\ e_{n21} & e_{n22} & e_{n23} \\ e_{n31} & e_{n32} & e_{n33} \end{bmatrix}$$

A transfer matrix T[i][j] which is to be used in later on calculation can be obtained from:

$$T_{[i][j]}=e_{n[i]} \cdot e_{p[j]} \quad \forall i,j \in \{1,2,3\}$$

another matrix ortho_OV[i][j] which is to be used also can be defined as:

$$\text{ortho\_OV}_{[i][j]} = e_{I[i]} \cdot e_{I[j]} \quad \forall i,j \in \{1,2,3\}$$

and since roll($\alpha$), pitch($\beta$), yaw($\gamma$) are used to define probe orientation, ortho_OV[i][j] can be also described by:

$$\text{ortho\_OV}[1][1] = \cos(\alpha)\cos(\gamma) - \sin(\alpha)\sin(\beta)\sin(\gamma)$$

$$\text{ortho\_OV}[1][2] = \cos(\alpha)\sin(\gamma) - \sin(\alpha)\sin(\beta)\cos(\gamma)$$

$$\text{ortho\_OV}[1][3] = -\sin(\alpha)\cos(\beta)$$

$$\text{ortho\_OV}[2][1] = -\cos(\beta)\sin(\gamma)$$

$$\text{ortho\_OV}[2][2] = \cos(\beta)\cos(\gamma)$$

$$\text{ortho\_OV}[2][3] = \sin(\beta)$$

$$\text{ortho\_OV}[3][1] = \sin(\alpha)\cos(\gamma) + \cos(\alpha)\sin(\beta)\sin(\gamma)$$

$$\text{ortho\_OV}[3][2] = \sin(\alpha)\sin(\gamma) - \cos(\alpha)\sin(\beta)\cos(\gamma)$$

$$\text{ortho\_OV}[3][3] = \cos(\alpha)\cos(\beta)$$

An orthogonal vector matrix can therefore be calculated by matrix multiplication of previous defined matrix T and ortho_OV:

$$ov = T * \text{ortho\_OV}$$

The theoretical magnetic field for an orthogonal system generated at sensor position pointing to $e_{I[i]}$ direction can be expressed (in short form) as:

$$f[\text{coil}][i](x,y,z,\alpha,\beta,\gamma)$$

after non_orthogonality correction (sensors may not be perpendicular to each other), the magnetic field sensor measures should be:

$$B[\text{sensor}][\text{coil}] = \sum_{i=1}^{3} f[\text{coil}][i](x,y,z,\alpha,\beta,\gamma) \times ov^{-1}[i][\text{sensor}]$$

Assume the real field sensor detected when coil is on is B'[sensor][coil], then:

$$B'[\text{sensor}][\text{coil}] - B[\text{sensor}][\text{coil}] = 0.0$$

Therefore, the 12 equation to be solved for x, y, z, $\alpha$, $\beta$, $\gamma$, are:

$$B'[\text{sensor1}][\text{coil1}] - \sum_{i=1}^{3} f[\text{coil1}][i](x,y,z,\alpha,\beta,\gamma) \times ov^{-1}[i][\text{sensor1}] = 0.0$$

$$B'[\text{sensor1}][\text{coil2}] - \sum_{i=1}^{3} f[\text{coil2}][i](x,y,z,\alpha,\beta,\gamma) \times ov^{-1}[i][\text{sensor1}] = 0.0$$

$$B'[\text{sensor1}][\text{coil3}] - \sum_{i=1}^{3} f[\text{coil3}][i](x,y,z,\alpha,\beta,\gamma) \times ov^{-1}[i][\text{sensor1}] = 0.0$$

$$B'[\text{sensor1}][\text{coil4}] - \sum_{i=1}^{3} f[\text{coil4}][i](x,y,z,\alpha,\beta,\gamma) \times ov^{-1}[i][\text{sensor1}] = 0.0$$

$$B'[\text{sensor2}][\text{coil1}] - \sum_{i=1}^{3} f[\text{coil1}][i](x,y,z,\alpha,\beta,\gamma) \times ov^{-1}[i][\text{sensor2}] = 0.0$$

$$B'[\text{sensor2}][\text{coil2}] - \sum_{i=1}^{3} f[\text{coil2}][i](x,y,z,\alpha,\beta,\gamma) \times ov^{-1}[i][\text{sensor2}] = 0.0$$

-continued $$B'[\text{sensor2}][\text{coil3}] - \sum_{i=1}^{3} f[\text{coil3}][i](x,y,z,\alpha,\beta,\gamma) \times ov^{-1}[i][\text{sensor2}] = 0.0$$

$$B'[\text{sensor2}][\text{coil4}] - \sum_{i=1}^{3} f[\text{coil4}][i](x,y,z,\alpha,\beta,\gamma) \times ov^{-1}[i][\text{sensor2}] = 0.0$$

$$B'[\text{sensor3}][\text{coil1}] - \sum_{i=1}^{3} f[\text{coil1}][i](x,y,z,\alpha,\beta,\gamma) \times ov^{-1}[i][\text{sensor3}] = 0.0$$

$$B'[\text{sensor3}][\text{coil2}] - \sum_{i=1}^{3} f[\text{coil2}][i](x,y,z,\alpha,\beta,\gamma) \times ov^{-1}[i][\text{sensor3}] = 0.0$$

$$B'[\text{sensor3}][\text{coil3}] - \sum_{i=1}^{3} f[\text{coil3}][i](x,y,z,\alpha,\beta,\gamma) \times ov^{-1}[i][\text{sensor3}] = 0.0$$

$$B'[\text{sensor3}][\text{coil4}] - \sum_{i=1}^{3} f[\text{coil4}][i](x,y,z,\alpha,\beta,\gamma) \times ov^{-1}[i][\text{sensor3}] = 0.0$$

A well-known non-linear least square equation solver can be applied to solve the above equations and find probe position x, y, z and orientation $\alpha$, $\beta$, $\gamma$. For example, Broyden and Levenberg-Marquardt's methods provide least squares solutions of a system of overdetermined nonlinear equations.

As stated above, one position determining method that can be used to determine the position of the probe sensing the magnetic field components generated by the coils involves solving an overdetermined system of equations, using a standard nonlinear least squares minimization algorithm, such as the Gauss algorithm or the Levenberg-Marquardt algorithm, known by those skilled in the art. Starting from an initial guess, these algorithms iteratively improve on the guess by a well-known and well-defined procedure. In the preferred embodiment using four coils, there would be twelve nonlinear equations with six unknowns. The unknown variables include the position vector of the probe, and its orientation parameterized as roll, pitch and yaw angles. The expressions to be set to zero are the differences of the measured field that each sensor on the probe measures for each coils activation mode, minus the theoretically calculated value for the same sensor and coil activation mode, given an arbitrary position and orientation. Using this approach, the geometric characteristics of the probe itself, namely the distance offset of each sensor to a reference point, preferably the tip of the probe, as well as the deviation of the probe's reference frame from being orthogonal, can be accounted for.

Provided that the probe stays within the geometry of the overlapping coils, the generated field from the coils advantageously behaves in a quasi-linear manner on planes of constant distance from the plane containing the coils. Namely, the magnetic fields each have at least one nonzero component with magnitude which is constant, linear or nearly linear, with respect to distance in a reference direction within the sensing volume.

The use of the near-field has a number of advantages of field generation techniques that use dipole far-fields. For instance, better dynamic range is achieved since the magnetic fields do not drop as fast. There is also less sensitivity to coil imperfections. For example, a "bump" or imperfection on a small dipole field generating coil tends to create much larger error as compared to imperfections of equal dimensions on overlapping planar coils.

Another advantage of the present system is that it is more tolerant of the presence of metals near the coils. This is because when nearby metal acquires induced magnetism due to the coil activation, the metal behaves as a dipole field itself. Thus, if the field generated by the coils were a dipole field as well, the ratio of the field produced by the metal to the field produced by the coil would be constant. However, with the field generated by the present system's overlapping coils, the ratio drops with distance because the dipole field of the metal will drop faster than the field generated by the coils.

Yet another advantage of the present system is that the current needed to generate a given field levels at a point in space are greatly reduced as compared to those generated by dipoles.

As these and other variations and combinations of the features discussed above can be utilized without departing from the present invention as defined by the claims, the foregoing description of the preferred embodiments should be taken by way of illustration rather than by way of limitation of the present invention

What is claimed is:

1. Apparatus for determining the position of an object comprising:
   (a) a plurality of magnetic field generating coils for generating a plurality of different magnetic fields in a sensing volume, said coils being arranged in a stacked, overlapping group such that the sensing volume is positioned on one side of said overlapping group of coils taken together and not between any of said coils;
   (b) control means for actuating said coils to generate said magnetic fields in a predetermined sequence,
   (c) a sensor connected to the object and movable within said sensing volume, and adapted to detect magnetic field components in at least two different local directions relative to the sensor, and
   (d) calculation means for determining the position of said sensor from the magnetic field components detected by said sensor during generation of said magnetic fields.

2. Apparatus as claimed in claim 1, further comprising control means for generating a plurality of successive magnetic fields within said sensing volume, said control means being operative to actuate said coils to generate said magnetic fields in sequence, said calculation means being operative to determine the position of said object within said sensing volume from said magnetic field components detected during generation of said magnetic fields.

3. Apparatus as claimed in claim 2, wherein said coils are formed from a plurality of conductor segments, and said calculation means calculates the magnetic field contribution B of each said conductor segment in accordance with the equation:

$$|B(x,y,z)|=I(\cos(A1)+\cos(A2))/(cR)$$

where I is the current through said conductor segment, c is the speed of light, R is the distance between the location of the sensor at point r=(x,y,z) and said conductor segment, A1 is the angle between the sensor and one end of said conductor segment, and A2 is the angle between the sensor and the other end of said conductor segment.

4. Apparatus as claimed in claim 3, wherein said conductor segments of each said source form a polygonal shape.

5. Apparatus as claimed in claim 4, wherein said conductor segments of each said source form a triangular shape.

6. Apparatus as claimed in claim 5, wherein said conduct segments form an isosceles triangle.

7. Apparatus as claimed in claim 5, wherein said plurality of coils comprises three coils.

8. Apparatus as claimed in claim 5, wherein said plurality of coils comprises four coils.

9. Apparatus as claimed in claim 8, wherein said coils are arranged to overlap one another in horizontal extent to produce a eight-pointed star.

10. Apparatus as claimed in claim 5, wherein the conductor segments are rectangular in cross-section.

11. Apparatus as claimed in claim 5, wherein said coils have center points which are spaced apart from one another at a center distance.

12. Apparatus as claimed in claim 11, wherein said center distance is about 10 cm.

13. Apparatus as claimed in claim 5, wherein said sensing volume extends outwardly to a maximum distance of interest, and the ratio of said maximum distance of interest to an effective diameter of said coils is less than or equal to two, said effective diameter comprising a diameter of a circle circumscribing said coils.

14. Apparatus as claimed in claim 1, wherein said plurality of coils comprises at least two said coils, and said apparatus further includes dipole means for generating one or more magnetic dipole fields within said sensing volume, said calculation means being further operative to determine the position of said probe within said sensing volume from said magnetic field components detected by said sensor during generation of said magnetic fields by said coils and magnetic field components detected by said sensor from said dipole means.

15. Apparatus for determining the position of an object comprising:
   (a) a plurality of magnetic field generating coils for generating a plurality of different magnetic fields in a sensing volume, said coils being arranged in a stacked, overlapping group such that the sensing volume is positioned on one side of said overlapping group of coils taken together and not between any of said coils, each of said coils including conductors encompassing an enclosed area, said coils being positioned so that said enclosed areas of said coils at least partially overlap one another in horizontal extent and define an overlap area, said overlap area encompassing at least about fifty percent of the enclosed area of each of said coils;
   (b) control means for actuating said coils to generate said magnetic fields in a predetermined sequence;
   (c) a sensor connected to the object and movable within said sensing volume, said sensor adapted to detect magnetic field components in at least two different local directions relative to the sensor; and
   (d) calculation means for determining the position of said sensor from the magnetic field components detected by said sensor during generation of said magnetic fields.

16. A method of determining the position of an object within a sensing volume comprising the steps of:
   (a) actuating a plurality of magnetic field-generating coils arranged in a stacked, overlapping group to generate a plurality of magnetic fields in a predetermined sequence such that at least two of said coils generate fields varying quasi-linearly with position within near-field volumes, the near-field volumes of said coils intersecting one another within a sensing volume positioned on one side of said overlapping group of coils taken together and not between any of said coils;
   (b) measuring magnetic field components in the sensing volume above the near-field areas of said coils in at least two different local directions relative to a sensor connected to the object during generation of said fields; and
   (c) determining the position of said sensor from said magnetic field components detected during generation of said magnetic fields.

17. A method a claimed in claim 16, wherein said coils are formed from a plurality of conductor segments, and said step of determining the position of said sensor includes the step of calculating magnetic field contributions of each of said conductor segments of said coils.

18. A method as claimed in claim 17, wherein said step of calculating comprises calculating the magnetic field contribution B of each said conductor segment in accordance with the equation:

$$|B(x,y,z)|=I(\cos(A1)+\cos(A2))/(cR)$$

where I is the current through said conductor segment, c is the speed of light, R is the distance between the location of the sensor at point r=(x,y,z) and said conductor segment, A1 is the angle between the sensor and one end of said conductor segment, and A2 is the angle between the sensor and the other end of said conductor segment.

19. A method of determining the position of an object within a sensing volume comprising the steps of:

(a) generating a plurality of different magnetic fields in a predetermined sequence in the sensing volume from a plurality of magnetic field generating coils arranged in a stacked, overlapping group such that the sensing volume is positioned on one side of said overlapping group of coils taken together and not between any of said coils;

(b) measuring magnetic field components of said magnetic fields generated from said plurality of coils in at least two different local directions relative to a sensor connected to the object during generation of said fields; and (c) determining the position of said sensor from said magnetic field components detected during generation of said magnetic fields.

20. A method of determining the position of an object within a sensing volume comprising the steps of:

(a) generating a plurality of different magnetic fields in a predetermined sequence in the sensing volume from a plurality of magnetic field generating coils arranged in a stacked, overlapping group such that the sensing volume is positioned on one side of said overlapping group of coils taken together and not between any of said coils;

(b) generating one or more magnetic dipole fields within said sensing volume;

(c) measuring magnetic field components of said generated magnetic fields in at least two different local directions relative to a sensor connected to the object during generation of said fields; and (d) determining the position of said object from the magnetic field components detected during generation of said magnetic fields.

21. Apparatus for generating magnetic fields inside the body of a patient, comprising a plurality of magnetic field generating coils for generating a plurality of different magnetic fields in a sensing volume, said coils being arranged in a stacked, overlapping group such that the sensing volume is positioned on one side of said overlapping group of coils taken together and not between any of said coils.

* * * * *

UNITED STATES PATENT AND TRADEMARK OFFICE
CERTIFICATE OF CORRECTION

PATENT NO. : 5,752,513
DATED : May 19, 1998
INVENTOR(S) : Acker et al.

It is certified that error appears in the above-identified patent and that said Letters Patent is hereby corrected as shown below:

Col. 2, line 25, after "produce" change "a" to -- an --.
Col. 2, line 58, after "sensing" insert -- volume --.
Col. 3, line 6, before "intersecting" insert -- coils --.
Col. 3, line 21, change "segment" to -- segments --.
Col. 4, line 42, change "segments" to -- segment --.
Col. 5, line 20, after "diameter of the" insert -- coils --.
Col. 6, line 46, after "first rotation" change "a s" to -- as --.
Col. 9, line 26, change "depictions" to -- depiction --.
Col. 12, line 10, change "use" to -- used --.
Col. 14, line 50, change "nonzero" to -- non-zero --.
Col. 15, line 15, after "invention" insert a period.
Col. 15, line 67, after "produce" change "a" to -- an --.
Col. 17, line 1, after "method" change "a" to --as --.

Signed and Sealed this

First Day of September, 1998

Attest:

BRUCE LEHMAN

*Attesting Officer*     *Commissioner of Patents and Trademarks*